United States Patent
Misumi et al.

(10) Patent No.: US 6,524,612 B2
(45) Date of Patent: Feb. 25, 2003

(54) ADHESIVE COOLING COMPOSITION AND PROCESS FOR ITS PREPARATION

(75) Inventors: Manabu Misumi, Osaka (JP); Motoko Yamashita, Osaka (JP)

(73) Assignee: Kobayashi Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 09/726,121

(22) Filed: Nov. 30, 2000

(65) Prior Publication Data

US 2001/0000029 A1 Mar. 15, 2001

Related U.S. Application Data

(62) Division of application No. 09/042,891, filed on Mar. 17, 1998, now Pat. No. 6,224,899.

(30) Foreign Application Priority Data

Mar. 18, 1997 (JP) .............................................. 9-64201
Mar. 3, 1998 (JP) .............................................. 10-50286

(51) Int. Cl.⁷ .............................................. A61L 15/00
(52) U.S. Cl. ...................................................... 424/448
(58) Field of Search ......................................... 424/448

(56) References Cited

U.S. PATENT DOCUMENTS 5,780,047 A    7/1998    Kamiya et al. ............. 424/443

FOREIGN PATENT DOCUMENTS

| JP | 61-41926 | 9/1986 | | |
| JP | 61-260007 | 11/1986 | | |
| JP | 63-15243 | 4/1988 | | |
| JP | 3-16989 | 3/1991 | | |
| JP | 3-33686 | 5/1991 | | |
| JP | 3-38244 | 6/1991 | | |
| JP | 3-39043 | 6/1991 | | |
| JP | 3-161436 | 7/1991 | | |
| JP | 3-62693 | 9/1991 | | |
| JP | 3-64483 | 10/1991 | | |
| JP | 4-39379 | 2/1992 | | |
| JP | 4-149136 A | * 5/1992 | .......... | A61K/35/78 |
| JP | 5-19528 | 3/1993 | | |
| JP | 7-39748 | 2/1995 | | |
| JP | 7-223938 | 8/1995 | | |
| JP | 7-94383 | 10/1995 | | |
| JP | 7-94583 | 10/1995 | | |

OTHER PUBLICATIONS

Database Derwent on East, AN 1992–223431, JP 04149136 A (Kureha Chem Ind Co Ltd), abstract, May 1992.*

* cited by examiner

*Primary Examiner*—Russell Travers
*Assistant Examiner*—Alysia Berman
(74) *Attorney, Agent, or Firm*—Sughrue Mion, PLLC

(57) ABSTRACT

The invention provides an adhesive cooling gel composition which stably contains a large amount of water and which is excellent in cooling effect and/or coolness-preserving effect, and a process for preparing the same. The composition comprises a polyacrylic acid compound, a polyvalent metal component and water, wherein the content of water is 75 to 95% by weight based on the cooling composition. Also disclosed are an adhesive cooling composition shaped into a sheet, and a process for preparing the adhesive cooling composition, the process being selected from processes given below in (1) to (3), each process including a step of mixing and dissolving the components of the composition and a deaerating step: (1) a process wherein an aqueous solution is deaerated and then the other components of the composition are mixed and/or dissolved; (2) a process wherein while an aqueous solution is deaerated, the other components of the composition are mixed and/or dissolved; or (3) a process wherein after the other components of the composition are mixed and/or dissolved, the obtained solution is deaerated.

14 Claims, 4 Drawing Sheets

ADHESIVE COOLING COMPOSITION AND PROCESS FOR ITS PREPARATION

This is a divisional of application Ser. No. 09/042,891 filed Mar. 17, 1998 now issued U.S. Pat. No. 6,224,899, the disclosure of which is incorporated herein by reference.

FIELD OF THE INVENTION

The present invention relates to an adhesive cooling composition to be directly or indirectly applied to a subject including humans to cool the subject due to its latent heat in vaporization of water and a process for preparing the composition.

BACKGROUND OF THE INVENTION

Conventional cooling bases for a cooling composition include, for example, gels or aqueous solutions of crosslinked polyethylene glycol (PEG), polyethylene oxide (PEO), polyvinyl alcohol (PVA), sodium carboxymethyl cellulose, polyacrylic acid, salts thereof, carboxyvinyl polymer (CVP) or the like.

The cooling composition is available in various forms such as a sheet having a cooling base sealed with a film of polyethylene, polypropylene or the like or a poultice comprising a non-woven fabric or like fabrics coated with a gel base. In recent years, a demand has been growing for poultice-type cooling products from the viewpoints of adhesion, fixation, convenience in use, heat-absorbing property and so on.

Generally the cooling base for use in such poultice-type cooling products are in the form of a gel which is superior in shape retentivity and adhesiveness. For this reason, it is very difficult to uniformly stir and knead the components of the cooling composition in the manufacture thereof. Because of this difficulty, there arise problems, for example, masses of components not dispersed well due to insufficient stirring and air bubbles incorporated into the gel base.

Attempts have been made in the art to overcome such problems using an organic solvent such as polyhydric alcohol in more than a specific amount to reduce the dispersion density of the base.

However, this method, although advantageous in giving a uniform gel composition, inevitably involves a decrease of water to be incorporated into the composition in an amount corresponding to the volume of the organic solvent, consequently failing to produce a cooling composition which can achieve a higher cooling effect.

SUMMARY OF THE INVENTION

The present invention was completed in view of the above situation.

It is an object of the present invention to provide an adhesive cooling composition in a gel form which stably contains a large amount of water and which is excellent in cooling effect and/or coolness-preserving effect.

The adhesive cooling composition of the invention is safely applicable without causing irritation to the subject to be cooled, especially human's skins. The composition which is adhesive by itself can be conveniently fixed to a substrate (a subject to be cooled, including humans) without use of an aid such as an adhesive tape. A further advantage is that even when directly applied to the surface of a substrate, preferably to human's skins, the composition can be removed without leaving any residue on the substrate.

It is another object of the invention to provide a process for preparing the foregoing adhesive cooling composition.

It is a further object of the invention to provide an adhesive cooling device in the form of a sheet which contains the above-mentioned cooling composition as a cooling base.

The present inventors conducted extensive research to prepare a uniform gel composition without giving masses of components not dispersed well due to insufficient stirring, when mixing a polyacrylic acid, a polyvalent metal and an aqueous solution. As a result, the inventors found that when the bubble component is removed from the aqueous solution by deaeration, stirring and kneading can be done with an improved efficiency and the components can be uniformly dispersed in the aqueous solution, whereby a uniform gel composition is obtained. The gel composition produced by this method has the components dispersed well in the aqueous solution and is uniform and substantially free of a bubble component, even if a conventional solvent such as polyhydric alcohol is used in a considerably low proportion to the aqueous solution (or even if such solvent is not used).

The adhesive cooling composition of the invention need not contain a solvent, e.g. polyhydric alcohol as an essential constituent (or it may contain a small amount of a solvent) and is free of air bubbles. Due to the absence of a solvent and freedom from air bubbles, a more amount of water can be accommodated in the cooling composition.

Based on the above-mentioned findings, the present inventors realized at once the increase of water content conventionally considered difficult, directing attention to both the production process and the formula and successfully developed an adhesive cooling composition having a high cooling effect.

DETAILED DESCRIPTION OF THE INVENTION

Figure 1:
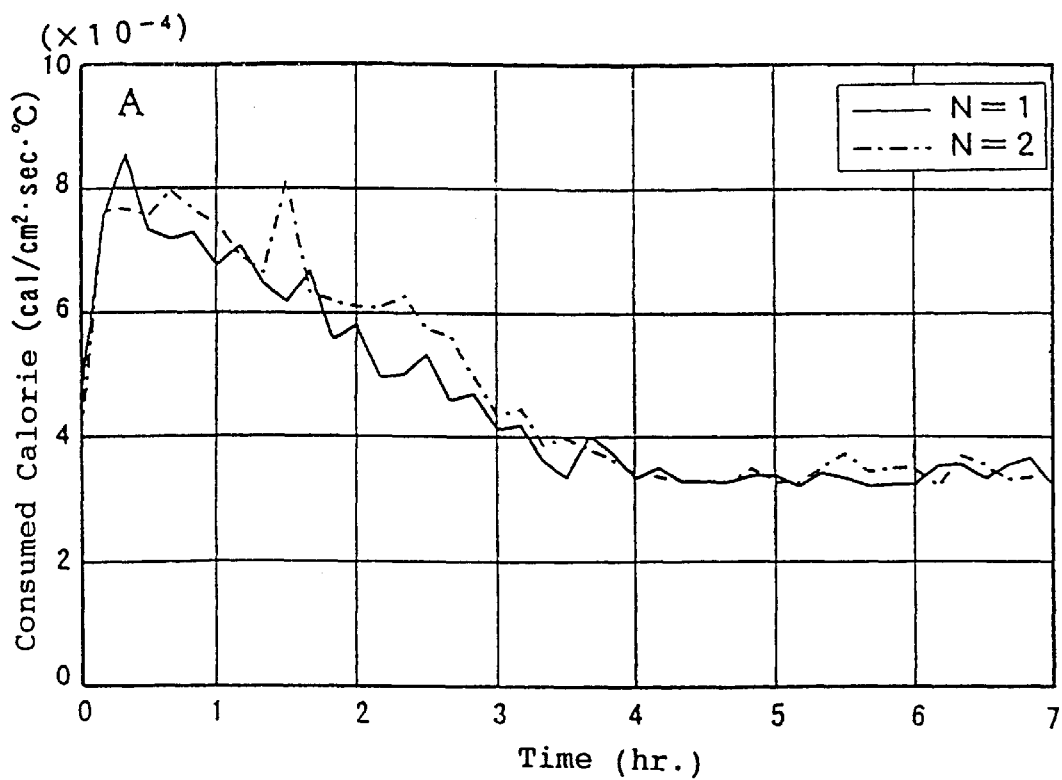
FIG. 1 is a graph showing the results of measuring the calories consumed by Plaster A of the invention (A in the graph) and by Plaster B of the invention (B in the graph) in Experiment Example 1. The lapse of time (hr) is plotted as the abscissa and the calorie ($\times 10^{-4}$) (cal/cm$^2$·sec·° C.) required to keep the hot plate constant at 37° C. was plotted as the ordinate.
Figure 1:
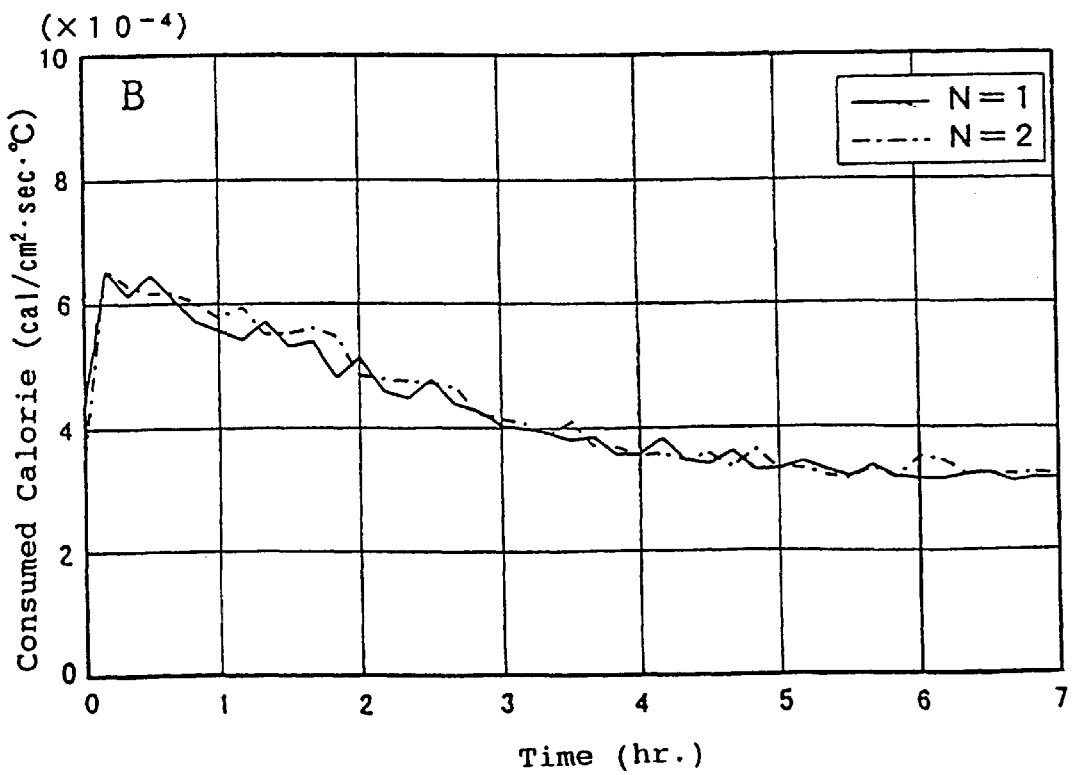

The adhesive cooling composition of the present invention comprises at least a polyacrylic acid compound, a polyvalent metal component and water, and the composition is characterized in that the composition contains water in an amount of 75 to 95% by: weight based on the cooling composition.

The term "polyacrylic acid compound" used herein includes salts of polyacrylic acids as well as polyacrylic acids.

Polyacrylic acids and salts of polyacrylic acids are usable irrespective of straight chain or branched chain form. The molecular weight of a polyacrylic acid compound to be used is not limited. Usually it has a molecular weight of 10,000 to 10,000,000. From the viewpoint of increasing the gel strength for the composition to stably hold more water, it is desirable to use a polyacrylic acid compound having a molecular weight of 1,000,000 to 7,000,000, preferably 4,000,000 to 6,000,000 (as determined by gel permeation chromatography (GPC)).

Suitable examples of the polyacrylic acid compound include partially crosslinked acrylic acid polymers (e.g. "Carbopol" (registered trademark), product of BF Goodrich Chemical Co.) as well as conventional polymers prepared by polymerization of acrylic acid.

Useful salts of polyacrylic acids are not limited. Preferred are monovalent metal salts of polyacrylic acids such as sodium polyacrylate, potassium polyacrylate and the like; amine polyacrylates such as monoethanolamine polyacrylate, diethanolamine polyacrylate, triethanolamine polyacrylate and the like; and ammonium salts of polyacrylic acids. These salts of polyacrylic acids can be used either alone or in combination. More preferred are alkali metal salts of polyacrylic acids such as sodium polyacrylate.

The above-mentioned polyacrylic acids and salts of polyacrylic acids can be used either alone or in combination. Generally the polyacrylic acid compound having a molecular weight of at least 1,000,000 is not easily available. Consequently it is desirable to use polyacrylic acids and salts of polyacrylic acids (such as sodium polyacrylate) in combination. However, if a polyacrylic acid compound with a molecular weight of at least 1,000,000 becomes easily available in future, the combined use would become unnecessary.

When the polyacrylic acid and a salt thereof are used in combination, their ratio is not limited insofar as the ratio is adjusted so that the combination has a molecular weight of at least 1,000,00, preferably at least 2,000,000, more preferably at least 4,000,000. The ratio (weight ratio) is, for example, in the range of from 0:10 to 9:1, preferably from 2:1 to 1:2.

The amount of the polyacrylic acid and/or a salt thereof used is 1 to 20% by weight, preferably 3 to 10% by weight, based on the cooling composition.

The term "polyvalent metal component" is used herein to include a broad range of species including polyvalent metals, salts thereof and polyvalent metal compounds.

The polyvalent metal component is not limited insofar as it has at least two valences and are capable of crosslinking the above-mentioned polyacrylic acids and/or salts of polyacrylic acids. The compounds as the polyvalent metal component can be used either alone or in combination.

Suitable examples of the polyvalent metal component are magnesium, calcium, zinc, cadmium, aluminum, titanium, manganese, cobalt, nickel and like polyvalent metals, their salts and their compounds. From the viewpoints of safety for skins, productivity and gel characteristics, it is preferred to use aluminum, magnesium, calcium or their compounds. Especially preferred are aluminum compounds.

Examples of useful aluminum compounds are hydroxides such as aluminum hydroxide; normal salts of inorganic or organic acids such as aluminum chloride, aluminum sulfate, aluminum acetate and aluminum stearate; basic salts thereof; double salts such as aluminum alum and potassium alum (potassium aluminum sulfate); aluminates such as sodium aluminate; inorganic aluminum complex salts; and organic aluminum chelate compounds. These aluminum compounds may be either soluble in water or sparingly soluble in water.

Useful magnesium compounds are, for example, magnesium hydroxide, magnesium carbonate, magnesium sulfate, magnesium nitrate, magnesium chloride and magnesium acetate. Useful calcium compounds are, for example, calcium hydroxide, calcium carbonate, calcium sulfate, calcium nitrate, calcium chloride, calcium acetate, calcium oxide and calcium phosphate.

The amount of the polyvalent metal component used is 0.01 to 20% by weight, preferably 0.01 to 10% by weight, more preferably 0.05 to 1% by weight, most preferably 0.1 to 0.5% by weight, based on the cooling composition.

The adhesive cooling composition of the invention contains water in addition to the above-mentioned components. The amount of water used is 75 to 95% by eight, preferably 81 to 95% by weight, more preferably 81 to 90% by weight, most preferably 81 to 85% by weight, based on the cooling composition.

The adhesive cooling composition of the invention is capable of gradually vaporizing water from the surface of the gel with time, and is therefore always maintained at a lower temperature than room temperature due to its latent heat, i.e. heat radiated in the vaporization of water. Consequently when the composition is applied to a subject, the subject is deprived of heat because of its latent heat of vaporization and is thereby cooled. In other words, the water contained in the composition is a source of cooling activity. Thus, the higher the water content is, the higher the cooling effect is.

The adhesive cooling composition comprising the above-mentioned components is in the form of a high molecular elastic gel, and is likely to contain air bubbles. The presence of such bubble component in the composition reduces the amount of water to be held by the composition per volume unit. Therefore, desirably the cooling composition of the invention is substantially free of a bubble component.

As described later in Experiment Example 1, when the cooling composition of the invention is substantially free of a bubble component, the composition can achieve a higher cooling effect, especially a higher quenching effect than compositions containing a bubble component, and is therefore very useful in fulfilling a quenching purpose.

The term "bubble component" used herein refers to a wide range of air bubbles including bubble gases as well as visually recognizable air bubbles.

The expression "substantially free of a bubble component" used herein means the absence of a bubble or the presence of a few bubbles, more specifically refers to a state in which no bubble is visually observable and no trace of broken bubbles exists on the surface of the gel or on the surface of a cut portion after processing the cooling composition.

The adhesive cooling composition of the invention comprises the above-mentioned components, and optionally may further contain at least one member selected from the group consisting of tartaric acid, citric acid, phosphoric acid, ethylenediaminetetraacetic acid and salts thereof.

These acids or salts thereof are useful for the following advantage. When combined with a polyvalent metal component, they can adjust the pH of the composition and can control the liberating rate (dissociation) of metal ions to bring the gel strength (crosslinking degree) to the desired range. Tartaric acid is preferred among them.

The amount of the foregoing acid or salt thereof used is suitably selected from the range of 0.01 to 5% by weight, preferably 0.05 to 0.5% by weight, based on the cooling composition.

Optionally the adhesive cooling composition of the invention may further contain a polyhydric alcohol.

Polyhydric alcohols are useful as a dispersing medium for polyacrylic acid or salts thereof, or as a binder in dispersing and/or emulsifying in water an oil component such as 1-menthol or the like, and are usable in moisturizing the composition and improving the comfortableness in use.

Polyhydric alcohols are not limited in terms of linear or branched chain form and molecular weight and can be any of species usually used which are safe for subjects.

Examples are glycerin, ethylene glycol, diethylene glycol, triethylene glycol, polyethylene glycol, propylene glycol, butylene glycol, polypropylene glycol, 1,3-propanediol, 1,4-butanediol, maltitol, xylitol and sorbitol. Among them, glycerin, propylene glycol and butylene glycol are suitable to use.

The amount of the polyhydric alcohol used is suitably selected from the range of 0.001 to 30% by weight, preferably 5 to 20% by weight, more preferably 10 to 20% by weight, based on the cooling composition. The use in an amount of less than 0.5% by weight is limitless.

Optionally the adhesive cooling composition of the invention may contain a cellulose derivative.

The cellulose derivative is useful in improving the processability of the composition of the invention which is a non-Newtonian fluid, in enhancing the stability of the gel and in facilitating the adjustment of viscosity.

There is no limitation on the cellulose derivatives to be used. Specific examples are carboxymethyl cellulose, hydroxymethyl cellulose, hydroxyethyl cellulose, hydroxypropyl cellulose, methyl cellulose, and alkali metal salts (sodium, potassium or the like) thereof and the like. These cellulose derivatives can be used either alone or in combination. Among them, carboxymethyl cellulose and alkali metal salts thereof are preferred.

The amount of the cellulose derivative used is suitably selected from the range of 0.01 to 10% by weight, preferably 0.1 to 5% by weight, more preferably 0.1 to 0.45% by weight, based on the cooling composition.

The adhesive cooling composition of the invention contains, as described above, water in a high proportion of at least 75% by weight based on the cooling composition, and therefore is excellent in heat-absorbing effect.

The adhesive cooling composition of the invention can stably hold a large amount of water and is not caused to ooze the water when compressed. Even if the composition has a water content of as high as 95% by weight, it is not rendered flowable when its viscosity is reduced, namely has an advantage of having shape retentivity. The composition even with a high water content is suitably elastic and highly adhesive and has a feature of being limitless in terms of subjects and locations to be applied.

The adhesive cooling composition of the invention is advantageous in:that it is easily removable from any subjects without leaving any residue on the subject and is highly safe.

Optionally the adhesive cooling composition of the invention may further contain a perfume such as peppermint oils, 1-menthol, linalool and linalyl acetate, antiseptics, humectants, irritation-relaxing agents, antimicrobial agents and the like.

A suitable adhesive cooling composition of the invention preferably contains at least one of linalool or linalyl acetate as a perfume in addition to the above components.

Any of linalool species extensively naturally occurring can be used irrespective of difference in structural isomers and in d-form or l-form. Preferred linalool is 1-linalool, such as one in a lavender oil. The linalyl acetate to be used can be any of the species extensively naturally occurring. These perfumes are not limited in terms of the origin.

The amount of the linalool used is 0.0005 to 0.6% by weight, preferably 0.002 to 0.45% by weight, more preferably 0.003 to 0.4% by weight, based on the cooling composition obtained as the end product.

The amount of the linalyl acetate used is 0.0005 to 0.8% by weight, preferably 0.002 to 0.7% by weight, more preferably 0.003 to 0.6% by weight, based on the cooling composition obtained as the end product.

The adhesive cooling composition of the invention may contain these components individually or as a mixture.

Among linalool species, d-linalool is contained in refined oils such as linaloe oils of Mexican growth, roosewood oils, coriander oils or Orth. linalooliferum Fujita, and 1-linalool is contained in refined oils such as hosho oils, lavender oils or bergamot oils. Linalyl acetate is contained in refined oils such as lavender oils, bergamot oils, petigrain oils, jasmine oils, ylan-ylan oils or lemon oils. Consequently these refined oils can be used as linalool or linalyl acetate insofar as they do not adversely affect the contemplated effect of the invention.

Lavender oils are suitable as such refined oils. Lavender oils contain, in addition to linalyl acetate and 1-linalool, hundreds of components such as geraniol, lavandulol, nerol, α-pinene, caryophyllene, 1,8-cineole, camphene, 1-limonene and dipennene. These components of the lavender oils are considered to cooperatively act for achieving the effect of the invention without adversely affecting the effect thereof.

Generally the lavender oil can be prepared, for example, by subjecting the flower ear of lavender to steam distillation or by extraction using a solvent such as hexane, petroleum ether, alcohol or the like.

The adhesive cooling composition of the invention may contain at least one of the lavender extracts prepared as above.

Lavenders usable in the invention are selected from a wide range of species including those pertaining to the genus Perilla frutescens crispd and their variety. Generally lavenders are classified as given below according to the shape of leaves and bracts: (1) Spica-type lavender group, (2) Stoechas-type lavender group, and (3) Fern-like lavender group (*Pterostachys lavender*). The lavender group (1) is sub-classified into *Lavandula angustifolia* Mill. species including their agricultural species, Lavandin type (*L.x intermedia* Emeric ex Loisel. (*Lavandula hybrida* Reverchon ex Briq., *L. ortensis* Hy)) and others (e.g. *L. latifolia* Medik. (*L. spica* auct., non L.)). Any of these lavenders can be used in the invention.

There is no limitation on lavenders in terms of the origin and the geographical region of growth. Useful lavenders can be any of those grown, e.g. in France, Italy, U.K., Russia, Australia, North America and Japan (Hokkaido).

Lavender extracts useful in the invention are not limited in terms of other components in the extract and their proportions insofar as the extract contains 5 to 60% by weight, preferably 20 to 45% by weight, of linalool or 5 to 80% by weight, preferably 20 to 70% by weight, of linalyl acetate.

It is desirable that the adhesive cooling composition of the invention contain 0.01 to 1% by weight, preferably 0.05 to 0.5% by weight, more preferably 0.1 to 0.3% by weight, of such lavender extract which, however, is not limitative.

The adhesive cooling composition of the invention containing any of these perfumes may further contain a surfactant. The surfactant to be used in the invention is suitably selected from any kind of surfactants including cationic, anionic, amphoteric and nonionic surfactants commonly used, according to the type of linalool or linalyl acetate to be contained in the composition of the invention and the type of perfume components of refined oils. These surfactants can be used either alone or in combination.

The adhesive cooling composition of the invention containing a perfume such as linalool or linalyl acetate can be effectively used especially for mammal animals including humans because of their undermentioned activities as well as the above-mentioned cooling activity.

When the adhesive cooling composition of the invention is directly or indirectly applied or pasted to the human body, the components of lavender extract such as linalool or linalyl acetate in the composition vaporize and effectively act through the nasal cavity, whereby the nerve is relaxed and the blood flow of peripheral skin is increased to elevate the temperature of peripheral skin, thereby promoting the radiation of heat from the inside of the body.

It is known that a specific correlation exists between the body temperature and sleep rhythm. Stated more specifically, the temperature of peripheral skin begins to rise just before falling asleep and a little later the rectal temperature is lowered. This state is retained during sleep ("Sogo Rinsho" vol.34, Special Number (1985), 14–16). It is suggested that the occurrence of body temperature rhythm just before falling asleep involves the mechanism for increasing the blood flow of skin to radiate the heat from the inside of the body. (Damm, F., Doring, G., et al "Body Temperature and Circadian Rhythm" 1973).

When the adhesive cooling composition of the invention is used, human biorhythm is artificially made close to natural body temperature rhythm in the beginning of sleep, whereby more natural sleep can be induced. The adhesive cooling composition of the invention allows the water held therein to evaporate from the surface with time as described above, and absorbs heat due to latent heat involved in vaporization. If the composition is applied or pasted to the skin before sleep, the skin is deprived of heat owing to latent heat of vaporization. The composition can promote the subject's activity of radiating heat from the body to smoothly induce sleep.

When the adhesive cooling composition of the invention is used, vaporizable components of lavender such as linalool or the like can tranquilize the subject when vaporized owing to the body temperature, namely can mentally assist the subject in inducing a peaceful sleep.

The adhesive cooling composition of the invention can be used to effectively act against insomnia or sleep-hindering trouble which is caused by mental factors such as anxiety, overwork, melancholy, excitement or the like, or by the irregularity of biorhythm.

The adhesive cooling composition of the invention can be prepared by a process comprising a step of mixing and/or dissolving the components of the composition and a deaerating step.

The mixing and/or dissolving step and the deaerating step are not limited in terms of the order and can be carried out in any order. For example, (i) before the components of the composition are mixed and/or dissolved, water or an aqueous solution may be deaerated; (ii) while water or an aqueous solution is deaerated, the other components of the composition are mixed with and/or dissolved in water or aqueous solution; or (iii) after the other components of the composition are mixed with and/or dissolved in water or an aqueous solution, the obtained solution is deaerated. When the composition contains vaporizable components, the process (i) or (ii) is preferred among these processes, and the process (i) is more preferred. In the case of the process (i) or (ii), after all of the components are added, they can be deaerated again in mixing them with stirring.

The deaeration method is not limited and is variously selected according to the subject to be treated and the treating stage. To avoid the increase of dispersion density of a solvent, it is preferred to conduct physical deaeration such as deaeration by mesh filtration and vacuum deaeration. The vacuum deaeration can be carried out, for example, by a closed vacuum method using a vacuum pump or a stirrer with a vacuum pump.

Stated more specifically, deaeration may be conducted, for example, using a stirrer with a vacuum pump at about 700 mmHg and at about 20 to about 30° C. for about 30 minutes for 1 liter of water or an aqueous solution used to which, however, the deaeration is not limited.

The method of stirring and kneading a solvent or an aqueous solution in the composition is not limited and can be carried out in the conventional manner, preferably using a twin-screw universal kneader, a twin-screw planetary mixer or equivalents thereof. These devices can be used over a wide range of stirring capability which enables the formation of low to high viscosity mass, and can satisfactorily cope with a rapid increase of viscosity occurring, e.g. in mixing a solvent system and an aqueous system. The devices are also beneficially operable without breakage of a gel by stirring and kneading on or after the formation thereof.

The adhesive cooling composition of the invention can be used mainly to partly cool the body part which is not limitative. For example, the composition can be applied to the forehead of a subject who is feverish, can cool body parts such as eyes, cheeks, jaws, legs, feet and the like which are locally in fever, or can cool inflammatory parts to assuage the pain when suffering from blow pain, sprain or muscular pain.

In application of the adhesive cooling composition of the invention containing a perfume such as linalool or the like, the vaporizable components of lavender are caused to act through the nasal cavity for the promotion of sleep inducement. For this purpose, the composition is preferably applied to body parts such as the upper half part in the neighborhood of the nose, preferably the breast or face and head, particularly the forehead.

According to the invention, there is also provided a cooling device (cooling article) which is produced by shaping the composition into a product in a specific shape according to the purpose of topical application.

While the cooling device is not limited in terms of a shape, a laminated sheet is preferred because it is easy to handle, portable and storageable. The laminated sheet can be produced by spreading the gel composition of the invention into a sheet or by applying the gel composition to a moisture-permeable sheet and spreading the composition. The latter form, i.e. a laminate sheet of a layer of gel composition laminated on a moisture-permeable sheet, is preferred from the viewpoints of handleability and convenient use.

There is no restriction on moisture-permeable sheets insofar as they can support the adhesive cooling composition and they have such suitable gas moisture permeability that they do not hinder the passage of a gas and vapor according to the moisture-releasing property of the composition and the vapor transmission of vaporizable components of a perfume such as linalool. Examples of useful sheets include various woven fabrics, non-woven fabrics and films. Insofar as the sheet has said properties, the pore diameter of the sheet is not limited, and is about 0.001 to about 5 mm, preferably about 0.01 to about 1 mm.

When the substrate is made of woven fabrics or non-woven fabrics, the raw materials thereof are not limited. Specific examples are natural fibers such as cotton, flax, wool and the like; cellulose fibers such as rayon, acetate and the like; and synthetic fibers such as nylon, vinylon, styrol, polypropylene, polyethylene, polyethylene terephthalate, acryl and the like.

When a film is used as the substrate, the raw materials are not limited. Examples are styrol, polypropylene, polyethylene terephthalate and polyethylene. A mesh film can be used to assure suitable permeability and moisture-permeability. The pore diameter of the mesh film is not limited but is 0.001 to 5 mm, preferably 0.01 to 1 mm as described above.

The thickness of the moisture-permeable substrate is not limited insofar as it does not hinder the passage of a vapor based on the moisture-releasing property of the composition. The thickness is 1 to 1000 $\mu$m, preferably 10 to 500 $\mu$m from the viewpoints of convenience in use and amenability to the site of application.

It is desirable that the substrate have suitable elasticity sufficient to become amenable to the external shape at the site of application on application of the cooling device to the skin.

The thickness of the adhesive cooling composition laminated on the moisture-permeable substrate is not limited, and is 10 to 10,000 $\mu$m, preferably 500 to 5,000 $\mu$m, more preferably 1,000 to 4,500 $\mu$m from the viewpoints of convenience in use, the amount of heat absorption and the like.

The amount of the composition to be laminated is not limited. It is desirable to apply and spread 50 to 200 g, preferably 100 to 150 g, of the composition per square meter of the moisture-permeable substrate.

The laminated sheet of the invention basically comprises a combination of the adhesive cooling composition and a moisture-permeable substrate, and optionally has a peelable film laminated on the surface of the adhesive cooling composition sheet. The peelable film is removed before use for the handleability and hygiene.

Such peelable film may be made of polyester, polypropylene, polyethylene, nylon, vinyl chloride, polyethylene terephthalate or the like.

The laminated sheet of the invention is not limited in terms of external shape (size and the like) and has an external shape (size and the like) suitably selected according to the subject, the site of application and the like.

The laminated sheet of the invention can be produced by conventional methods using the adhesive cooling composition prepared in the above-mentioned manner. For example, the composition of the invention is uniformly spread on a peelable sheet to form a layer, and the moisture-permeable sheet is superposed on the layer. In this case, the laminated mass may be compressed by a roller to strengthen the fixation.

The laminated sheet of the invention not only can be applied to the forehead of a subject who is feverish, but also can be used as a device (article) for cooling body parts such as eyes, cheeks, jaws and other face portions, legs, feet and the like which are in fever. The laminated sheet also can temporarily cool body parts of inflammation caused by blow or sprain. The sheet can be used to cool down the muscles after playing sports. The sheet is useful also because it is immediately applicable without trouble and is disposable.

The laminated sheet of the invention prepared from the composition containing a perfume such as linalool and the like can absorb heat from the surface of skin and is useful as an aid or a sleep inducement promoting device capable of inducing sleep smoothly.

EXAMPLES

The present invention is described below in more detail with reference to the following examples, comparative examples and experiment examples to which, however, the invention is not limited.

Example 1

The adhesive cooling composition of the invention was prepared according to the following formula.

| Formula) | Sodium polyacrylate (molecular weight 5,000,000) | 7 w/w % |
|---|---|---|
| | Potassium alum | 0.2 |
| | Deionized water | 92.8 |
| | | 100 w/w % |

Production Method)

1. Deionized water (0.928 liter) was placed into a stirring kneader and was vacuum-defoamed using a mixer with a vacuum-defoaming ability for about 30 minutes (about 30° C.).

2. Sodium polyacrylate and potassium alum were mixed and were added to the kneader described above in item 1 while the mixture was stirred and kneaded in a manner to avoid the formation of powder masses.

3. After addition, while the mixture was vacuum-defoamed, stirring and kneading were carried out for an optional time until the bubble component was substantially lost.

No bubble component was visible in the obtained adhesive cooling composition and no trace of bubble was found on the surface of a cut portion of the cooling device of the composition.

Example 2

The adhesive cooling composition of the invention was prepared according to the following formula.

| Formula) | Sodium polyacrylate (molecular weight 5,000,000) | 7 w/w % |
|---|---|---|
| | Aluminum hydroxide | 0.2 |
| | Tartaric acid | 0.3 |
| | Deionized water | 92.5 |
| | | 100 w/w % |

Production Method)

1. Deionized water (0.925 liter) was placed into a stirring kneader and tartaric acid was added. The mixture was vacuum-defoamed using a mixer with a vacuum-defoaming ability for about 30 minutes (about 30° C.).
2. Sodium polyacrylate and aluminum hydroxide were mixed and were added to the kneader described above in item 1 while the mixture was stirred and kneaded in a manner to avoid the formation of powder masses.
3. After addition, while the mixture was vacuum-defoamed, stirring and kneading were carried out for an optional time until the bubble component was substantially lost.

No bubble component was visible in the obtained adhesive cooling composition and no trace of bubble was found on the surface of a cut portion of the cooling device of the composition.

Example 3

The adhesive cooling composition of the invention was prepared according to the following formula.

| Formula) | Sodium polyacrylate (molecular weight 5,000,000) | 5 w/w % |
|---|---|---|
| | Aluminum hydroxide | 0.2 |
| | Tartaric acid | 0.25 |
| | Concentrated glycerin | 10 |
| | Deionized water | 84.55 |
| | | 100 w/w % |

Production Method)

1. Sodium polyacrylate, aluminum hydroxide and concentrated glycerin were placed into a stirring kneader and uniformly dispersed.
2. A solution of tartaric acid in deionized water was gradually added to the kneader described above in item 1 while the mixture was stirred and kneaded.
3. After addition, while the mixture was vacuum-defoamed using a mixer with a vacuum-defoaming ability, stirring and kneading were carried out (about 30° C.) for an optional time until the bubble component was substantially lost.

No bubble component was visible in the obtained adhesive cooling composition and no trace of bubble was found on the surface of a cut portion of the cooling device of the composition.

Example 4

Each of the adhesive cooling compositions prepared in Examples 1 to 3 was spread over a piece of flannel, non-woven fabric or cloth, was cut into a suitable size and was sealed into a bag made of aluminum to give a sheet of adhesive cooling composition.

No bubble component was visible in the adhesive cooling device thus prepared, or no trace of bubble was found on the surface of a cut portion of the sheet of the composition.

Example 5

An adhesive cooling composition was prepared according to the same formula by the same process as in Example 3 with the exception of not carrying out the vacuum deaeration in the process.

A bubble component was visible in the adhesive cooling composition thus prepared, or a trace of broken bubbles was found on the gel and a trace of bubbles on the surface of a cut portion of the cooling device of the gel composition.

Example 6

The adhesive cooling composition of the invention was prepared according to the following formula. The amounts of the components shown in the formula are those of the final composition obtained after deaeration (the same in subsequent examples).

| Formula) | Sodium polyacrylate (molecular weight 5,000,000) | 6 w/w % |
|---|---|---|
| | Aluminum hydroxide | 15 |
| | Tartaric acid | 0.3 |
| | Methylparaben | 0.2 |
| | Natural perfume (Refined oil of common lavender) | 0.5 |
| | Deionized water | 78.0 |
| | | 100 w/w % |

Production Method)

1. Deionized water and tartaric acid were placed into a stirring kneader and dissolved.
2. Sodium polyacrylate, aluminum hydroxide, methylparaben and lavender were mixed and were added to the kneader described above in item 1 in a manner to avoid the formation of powder masses.
3. After addition, the mixture was vacuum-defoamed for a few minutes.

Example 7

The adhesive cooling composition of the invention was prepared according to the following formula.

| Formula) | Sodium polyacrylate (molecular weight 5,000,000) | 5 w/w % |
|---|---|---|
| | Aluminum hydroxide | 0.2 |
| | Tartaric acid | 0.25 |
| | Concentrated glycerin | 10.0 |
| | Natural perfume (refined oil of lavender) (Linalool 20% Linalyl acetate 50% Other refined oil components 30%) | 0.1 |
| | Deionized water | 84.45 |
| | | 100 w/w % |

Production Method)

1. Deionized water and tartaric acid were placed into a stirring kneader and dissolved.
2. Sodium polyacrylate, aluminum hydroxide and lavender extract were mixed with concentrated glycerin.
3. The mixture obtained above in item 1 was gradually added to the mixture obtained above in item 2.
4. After addition, the mixture was vacuum-defoamed for a few minutes.

Example 8

The adhesive cooling composition of the invention was prepared according to the following formula.

| Formula) | Sodium polyacrylate (molecular weight 5,000,000) | 7 w/w % |
| --- | --- | --- |
| | Aluminum hydroxide | 0.2 |
| | Tartaric acid | 0.3 |
| | Synthetic perfume (lavender) (Linalool 25% Linalyl acetate 45% Other refined oil components 30%) | 0.3 |
| | Deionized water | 92.2 |
| | | 100 w/w% |

Production Method)
1. Deionized water and tartaric acid were placed into a stirring kneader and dissolved.
2. Sodium polyacrylate, aluminum hydroxide and lavender extract were mixed together and were added to the kneader described above in item 1 in a manner to avoid the formation of powder masses.
3. After addition, the mixture was vacuum-defoamed for a few minutes.

Example 9

The adhesive cooling composition of the invention was prepared according to the following formula.

| Formula) | Sodium polyacrylate (molecular weight 5,000,000) | 7 w/w % |
| --- | --- | --- |
| | Polyvinyl alcohol | 10 |
| | Carboxyvinyl polymer | 3 |
| | Aluminum hydroxide | 0.2 |
| | Tartaric acid | 0.2 |
| | Synthetic perfume (refined oil of lavender) (Linalool 35% Linalyl acetate 40% Other refined oil components 30%) | 0.2 |
| | Methylparaben | 0.1 |
| | Glycerin | 5.0 |
| | Deionized water | 74.3 |
| | | 100 w/w % |

Production Method)
1. Deionized water, carboxyvinyl polymer, polyvinyl alcohol and tartaric acid were placed into a stirring kneader and dissolved.
2. Sodium polyacrylate, aluminum hydroxide, lavender and methylparaben were mixed with glycerin.
3. The mixture obtained above in item 2 was added to the kneader described above in item 1 in a manner to avoid the formation of powder masses.
4. After addition, the mixture was vacuum-defoamed for a few minutes.

Examples 10 to 13

The adhesive cooling compositions prepared in Examples 6 to 9 (corresponding to Examples 10 to 13, respectively) were spread on a meshy substrate sheet (made of PET) of 0.1 to 1 mm in pore size, were cut to a suitable size (5×13 cm) and were sealed into a bag made of aluminum to give a laminated sheet (plaster).

Experiment Examples

Experiment Example 1

The adhesive cooling composition prepared in Example 3 was spread on a non-woven fabric piece in an amount of 125 g per square meter of the piece and was cut to a size (3 cm×3 cm) to produce a laminated sheet (Plaster A). Using the composition prepared in Example 5, a laminated sheet was produced in the same manner (Plaster B).

The obtained plasters were pasted to a hot plate at 37° C. and a calorie required to maintain the hot plate at a specific temperature (37° C.) was measured with time. The results Of Plaster A (present invention) are shown in FIG. 1A and the results of Plaster B (present invention) in FIG. 1B. The results show that both plasters produced a cooling effect. It was found that Plaster A free of a bubble component and with a higher water content per volume unit was superior in quenching effect.

Experiment Example 2

Plasters A and B used in Experiment Example 1 were fixed on the foreheads of 6 monitors. Then the temperature drop in the foreheads was measured and an average value was calculated. The results are shown in Table 1.

TABLE 1

| | 0.5 hr. | 1.0 hr. | 1.5 hr. | 2.0 hr. | 2.5 hr. |
| --- | --- | --- | --- | --- | --- |
| PL. A | 2.95° C. | 2.82° C. | 2.95° C. | 2.53° C. | 2.46° C. |
| PL. B | 2.28° C. | 1.85° C. | 1.75° C. | 1.08° C. | 0.38° C. |

PL. = Plaster

These results reveal that Plaster A free of a bubble component is superior in cooling effect to Plaster B containing a bubble component.

Experiment Example 3

Three persons were selected at random as the subject from adults who were wakeful and suffered from insomnia. The laminated sheet (plaster) prepared in Example 10 was applied to their foreheads before sleep. The test investigated how the plaster affected their sleep.

The sleep-inducing effect was evaluated according to the following 5-grade criteria. The evaluation was made compared with the subject's sleep-inducing level before application of the plaster.
Evaluation in Terms of Comfortable Sleep (Evaluation as to Whether the Subject Felt Himself or Herself Having or Not Having a Comfortable Sleep or the Like)
1. Felt having a comfortable sleep, 2. Felt having some sleep, 3. Hard to say which, 4. Felt having a little sleep, 5. Felt having no sleep.

The results are shown in Table 2.
Evaluation in Terms of Falling Asleep
1. Falling asleep easily, 2. Falling asleep relatively easily, 3. Hard to say which, 4. Not falling asleep easily, 5. Not falling asleep The results are shown in Table 2.

TABLE 2

| Evaluation | (1) | (2) | (3) | (4) | (5) | |
| --- | --- | --- | --- | --- | --- | --- |
| Good sleep | 1 | 2 | 0 | 0 | 0 | (Number of person) |
| Falling asleep | 1 | 2 | 0 | 0 | 0 | (Number of person) |

As apparent from the results in Table 2, when the lasters of the invention were used, a high sleep-inducing effect was achieved on any of subjects.

Experiment Example 4

Tests (1) to (3) given below were carried out to investigate the mental stability ((1) Kraepelin test, (2) checking an EEG) and the elevated temperature of peripheral skin which may have occurred when the subject was exposed to lavender fragrance and when the plasters of the invention were used.

(1) Kraepelin Test

Subjects were made to continuously carry out calculation tests. Thereafter the calculation efficiency and change of correctness ratio were investigated to evaluate the mental stability effect. Two groups of subjects were formed, each group consisting of 15 healthy adults aged 24 to 32. The group A was made to perform the following calculatory task in a chamber which was filled with a lavender smell given off at room temperature from a sheet of paper impregnated with refined oil of lavender. The group B was made to conduct the same calculation tests in an odorless chamber.

Calculation tests

Figure 2:
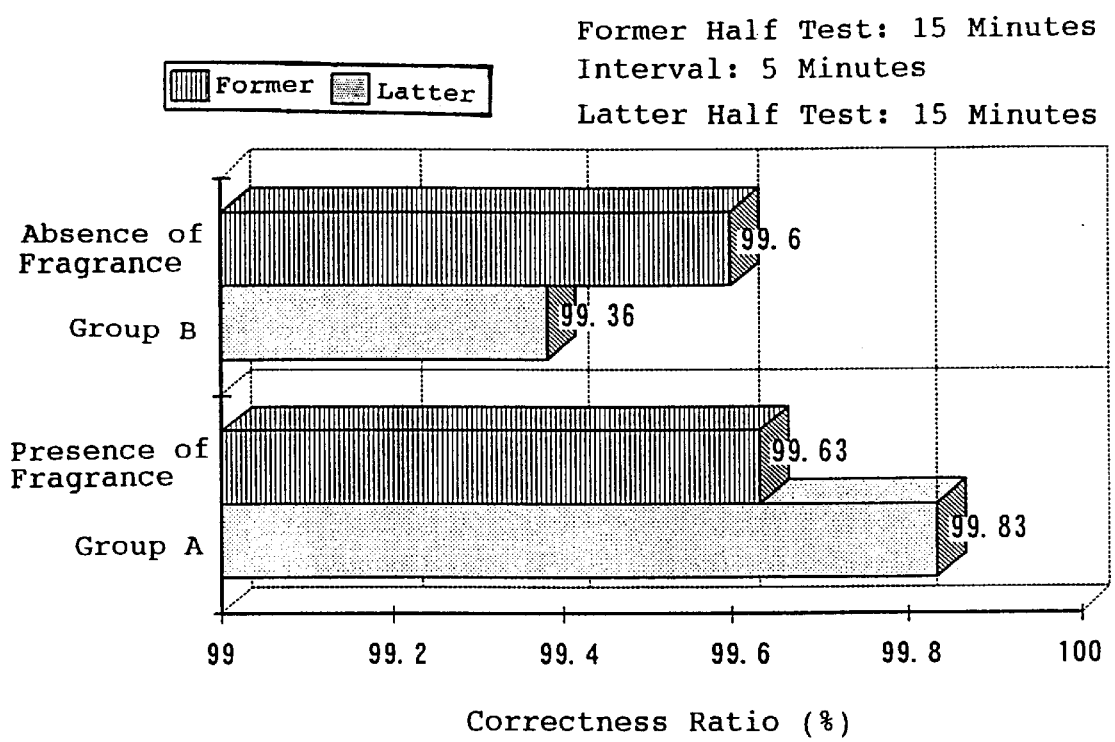
FIG. 2 shows the results, in comparison, of Kraepelin test carried out in the presence or absence of lavender fragrance in Experiment Example 4 (1).

The subjects were made (i) to add up two adjacent figures in rows of figures printed on both surfaces of a piece of paper, and (ii) to write with a pencil the answer into a space between the two adjacent figures below each row. When the total is a two-digit figure, the last figure of the two-digit figure was to be written. The subjects were made to resume the calculations in the next row when the supervisor called a signal after the lapse of one minute. The subjects were made to do the test of calculation volume on each surface of the paper in 15 minutes. A one-minute calculation operation was taken as one bout, and 15 bouts were continuously conducted without a break. The test work was carried out in the order of a 15-minute former half test, a 10-minute interval and a 15-minute latter half test. The test work was conducted twice (morning and afternoon) a day to confirm the difference in the work efficiency in the morning and the afternoon. The results are shown in FIG. 2.

The group B who worked in the odorless chamber performed the calculations at a lower correctness ratio in the latter half test than in the former half test (the ratio of the former being 99.6% against 99.38% as that of the latter), whereas the group A who worked in the chamber filled with the fragrance showed a higher correctness ratio in the latter half test than in the former half test (the ratio of the former being 99.63% vs. 99.83% as that of the latter). This means that the subjects of the group A became mentally stabilized when they worked smelling an aroma component in refined oil of lavender.

(2) Measurement with Electroencephalogram

The electroencephalogram (EEG) is a record of an electric activity of cerebral neurocytes. It is known that α-wave, i.e. one component of EEG, appears in an increased amount in a state of rest wherein we are consciously impressed with feeling mentally composed ("Influence of Aroma on Brain Function" Fragrance Journal, No. 9, 1989, pp.20–26). The repose effect can be evaluated by measuring the amount of a wave appearing in the EEG.

Experiment Method

The experiment was carried out with 6 subjects in a thermo-hygrostat.

The subjects were given a 20-minute rest. Then, the plaster prepared in Example 10 was applied to their foreheads and left there for 3 minutes. Thereafter the amount of α wave appearing in the EEG for 3 minutes was measured using a Bio amp 0523S (product of NF Kairo Co., Ltd.). The plaster prepared in Example 10 emitted lavender fragrance immediately after application.

Stated more specifically, electrodes were applied to two spots of subjects' foreheads to make an EEG at the two spots. After high-speed Fourier transformation, the amount of α wave appearing at a frequency of 8–13 Hz was taken out from the whole brain waves. In a control experiment, the amount of α wave appearing was determined in the same manner as above before application of the plaster to the subject.

Results

The results are shown as compared with the results of the control experiment.

Figure 3:
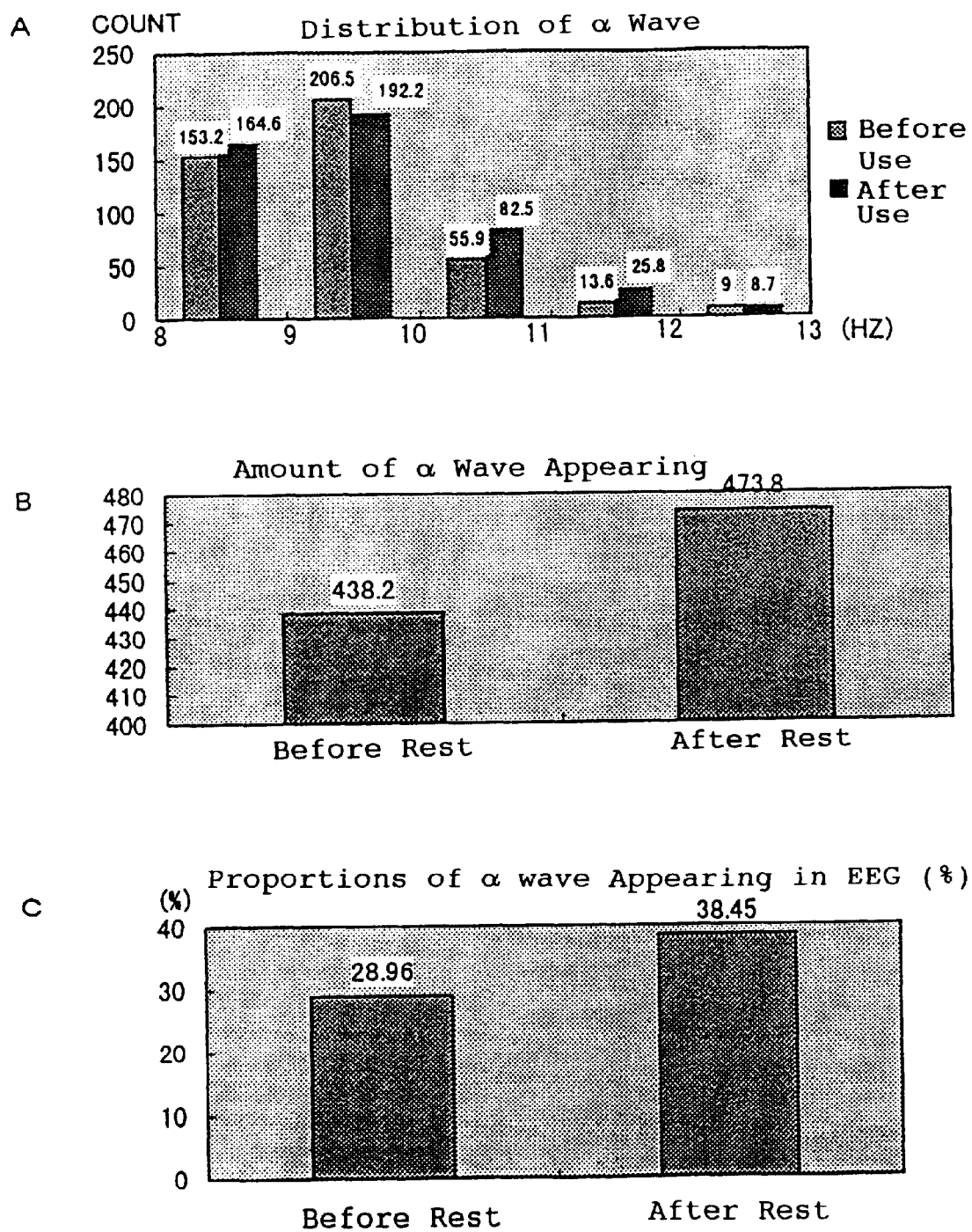
FIG. 3 is a graph showing the amount of α wave appearing when the plaster of the invention was used in Experiment Example 4 (2), compared with the case wherein the plaster thereof was not used. A graph A in FIG. 3 shows a detailed distribution of α wave at 8 to 13 HZ which was obtained by the analysis of electroencephalogram (EEG) at 8 to 13 HZ. A graph B in FIG. 3 shows the overall amounts of α wave appearing, in comparison between the data in the presence or absence of the plaster of the invention. A graph C in FIG. 3 shows the proportions of α wave in the EEG in its entirety (including the EEG outside 8–13 HZ region) in comparison between the data in the presence or absence of the plaster of the invention.

A graph A in FIG.3 shows a detailed distribution of α wave at 8 to 13 HZ which was obtained by the analysis of EEG at 8 to 13 HZ. The graph A indicates that the distribution of α wave shifted to the range of 10 to 12 HZ immediately after application of the plaster (poultice) to the subject in a awakened state. This denotes that when the plaster of the invention was applied, a soothing effect was produced. A graph B in FIG. 3 shows the overall amounts of α wave appearing, in comparison, in the presence or absence of the plaster of the invention. The figures (indices) in the graph are those for confirming the increase in the amount of α wave appearing, namely that the amount of α wave appearing was increased by application of the plaster of the invention. A graph C in FIG. 3 shows the proportions of α wave in the EEG in its entirety (including EEG outside 8–13 HZ region), in comparison, in the presence or absence of the plaster of the invention. This also verifies that the amount of α wave appearing is increased by application of the plaster of the invention.

As seen from the foregoing results, the amount of α wave appearing in the EEG increases when the plaster of the invention is applied, and a mentally stabilizing effect can be produced by the use thereof.

(3) Increase in Temperature of Peripheral Skin Surface

Experiment Method

The plaster of the invention prepared in Example 10 was applied to the foreheads of 6 subjects in a thermo-hygrostat. The distribution of temperature at subjects' palm of the hand was measured using a thermograph.

In a control experiment, the subjects were kept in a relaxed state for 20 minutes to confirm that the body temperature became constant. Thereafter, the distribution of temperature at subjects' palm of the hand was measured in a state of open eyes for 3 minutes (before rest, shown with a dotted line in a graph A) and then in a state of closed eyes for 3 minutes (after rest, shown with a solid line in the graph A).

Subsequently, 30 minutes later, the subjects were held again in a relaxed state. After confirming that the body temperature became constant, the distribution of temperature at subjects' palm of the hand was measured in a state of open eyes for 3 minutes (before rest, shown with a dotted line in a graph B) and then in a state of closed yes for 3 minutes after application of the plaster to the subjects' foreheads (after rest, shown with a solid line in the graph B).

Figure 4:
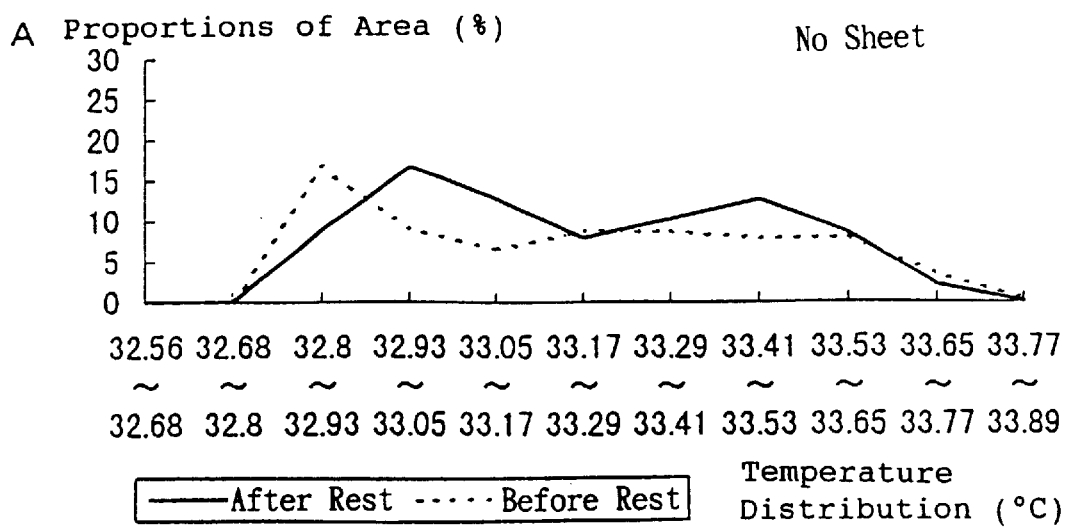
FIG. 4 shows an increase in the temperature of peripheral skin brought about by application of the plaster of the invention in Experiment Example 4 (3). A graph A in the figure shows the results of measuring the temperature of peripheral skin before rest (3 minutes, a dotted line) and after rest (for 3 minutes, a solid line) without application of the plaster of the invention. A graph B shows the results of measuring the temperature of peripheral skin before rest (3 minutes, a dotted line) without application of the plaster of the invention and after rest (3 minutes, a solid line) with the plaster of the invention applied.
Figure 4:
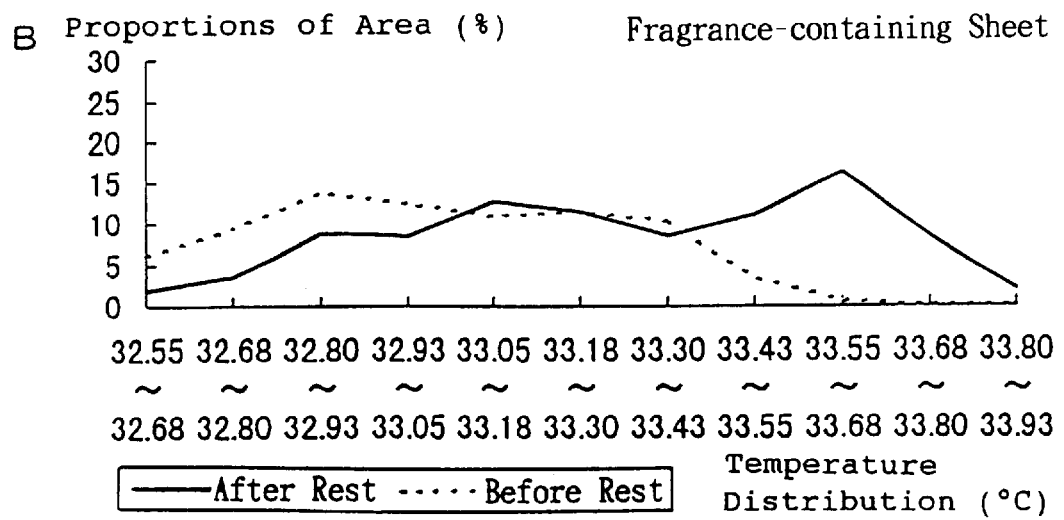

The results are shown in FIG. 4.

The proportions (%) of area at each temperature merely increased without shift of temperature distribution in a state of rest without the plaster fixed, as compared with the data before rest. On the other hand, the temperature distribution in a state of rest with the plaster fixed shifted to the right side (higher temperature) compared with the data before rest, and the temperature on the surface of skin was elevated. When the plaster was applied (shown with a solid line in the graph B), the proportions of area at high temperatures significantly increased compared with the data (shown with a solid line in the graph A) when the plaster was not applied. This means that when the plaster of the invention was used, the blood flow in the peripheral skin was increased, causing the radiation of heat from the body.

What we claim is:

1. A method of inducing sleep, comprising the step of attaching a laminate sheet to a human, wherein the laminate sheet comprises a moisture-permeable substrate in the form of a sheet and an adhesive cooling composition, further wherein the adhesive cooling composition comprises a polyacrylic acid compound, a polyvalent metal component and water, wherein the content of water is 75 to 95% by weight based on the adhesive cooling composition and the adhesive cooling composition is substantially free of a bubble component.

2. The method of inducing sleep according to claim 1, wherein the content of water is 81 to 95% by weight of the adhesive cooling composition.

3. The method of inducing sleep according to claim 1, wherein the polyacrylic acid compound accounts for 1 to 20% by weight and the polyvalent metal component accounts for 0.01 to 10% by weight of the adhesive cooling composition.

4. The method of inducing sleep according to claim 1, wherein the polyacrylic acid compound has an average molecular weight of 1,000,000 to 7,00,000.

5. The method of inducing sleep according to claim 1, wherein the polyacrylic acid compound is at least one member selected from the group consisting of polyacrylic acid, sodium polyacrylate, potassium polyacrylate, monoethanolamine polyacrylate, diethanolamine polyacrylate, triethanolamine polyacrylate and ammonium salt of polyacrylic acid.

6. The method of inducing sleep according to claim 1, wherein the polyvalent metal component is at least one member selected from the group consisting of magnesium compounds, calcium compounds, zinc compounds, cadmium compounds, aluminum compounds, titanium compounds, manganese compounds, cobalt compounds and nickel compounds.

7. The method of inducing sleep according to claim 1, wherein the adhesive cooling composition further contains at least one member selected from the group consisting of tartaric acid, citric acid, phosphoric acid, ethylenediaminetetracetic acid and salts thereof.

8. The method of inducing sleep according to claim 1, wherein the adhesive cooling composition further contains a polyhydric alcohol.

9. The method of inducing sleep according to claim 8, wherein the polyhydric alcohol is at least one member selected from the group consisting of glycerin, ethylene glycol, diethylene glycol, triethylene glycol, polyethylene glycol, propylene glycol and butylene glycol.

10. The method of inducing sleep according to claim 1, wherein the adhesive cooling composition further contains at least one cellulose derivative selected from the group consisting of carboxymethyl cellulose, hydroxymethyl cellulose, hydroxyethyl cellulose, hydroxypropyl cellulose, methyl cellulose, and alkali metal salts thereof.

11. The method of inducing sleep according to claim 10, wherein the cellulose derivative is at least one member selected from the group consisting of carboxymethyl cellulose, hydroxymethyl cellulose, hydroxyethyl cellulose, hydroxypropyl. cellulose, methyl cellulose and alkali metal salts thereof.

12. The method of inducing sleep according to claim 1, wherein the adhesive cooling composition further contains at least one of linalool or linalyl acetate.

13. The method of inducing sleep according to claim 12, wherein the adhesive cooling composition contains 0.0005 to 0.6% by weight linalool or 0.0005 to 0.8% linalyl acetate.

14. The method of inducing sleep according to claim 1, wherein the adhesive cooling composition further contains a lavender extract.

* * * * *